United States Patent [19]
Hadzic et al.

[11] Patent Number: 5,830,151
[45] Date of Patent: Nov. 3, 1998

[54] APPARATUS FOR LOCATING AND ANESTHETIZING PERIPHERAL NERVES A METHOD THEREFOR

[75] Inventors: Admir Hadzic, Montclair, N.J.; Jerry Vloka, New York, N.Y.

[73] Assignee: Innovative Design Associates, Upper Saddle River, N.J.

[21] Appl. No.: 968,816

[22] Filed: Nov. 26, 1997

Related U.S. Application Data

[63] Continuation of Ser. No. 419,419, Apr. 10, 1995, abandoned.

[51] Int. Cl.$^6$ ........................................................ A61B 5/00
[52] U.S. Cl. .............................................................. 600/554
[58] Field of Search ............................ 600/554; 607/118, 607/145

[56] References Cited

U.S. PATENT DOCUMENTS

| | | | |
|---|---|---|---|
| 3,682,162 | 8/1972 | Colyer . | |
| 4,515,168 | 5/1985 | Chester et al. | 128/741 |
| 4,824,433 | 4/1989 | Marz et al. | 128/741 |
| 5,115,705 | 5/1992 | Monte et al. | 84/617 |
| 5,284,153 | 2/1994 | Raymond et al. | 128/741 |

OTHER PUBLICATIONS

Raj. et al., "Use of the Nerve Stimulator for Peripheral Blocks" Regional Anesthesia, Apr.–Jun. 19990, pp. 14–21.

*Primary Examiner*—Max Hindenburg
*Attorney, Agent, or Firm*—Fitch, Even, Tabin & Flannery

[57] ABSTRACT

The present invention is directed to an apparatus for locating and anesthetizing peripheral nerves. The apparatus of the present invention enables an operator to independently complete a nerve blockade procedure, without the need for an assistant. The apparatus includes a generator which provides an electrical stimulus within a selected range. Adjustable control knobs located on the generator enable an operator to designate the selected amperage range. The apparatus is adapted for accepting a syringe for storing and administering anesthesia, and a tube for carrying the anesthesia from the syringe to a disposable anesthesia needle. An electronic cable connects the needle to the generator for delivering the electrical stimulus to the needle. The apparatus includes a remotely located foot pedal connected to the generator by a coupling cable, which enables the operator to control and modify the magnitude of the electrical stimulus. The addition of the pedal leaves the operator's hands free for unassisted nerve blockade procedure under sterile conditions. The present invention also discloses a method for operating the apparatus.

11 Claims, 3 Drawing Sheets

APPARATUS FOR LOCATING AND ANESTHETIZING PERIPHERAL NERVES A METHOD THEREFOR

This application is a continuation of Ser.No. 08/419,419 filed Apr. 10, 1995, now abandoned.

BACKGROUND OF THE INVENTION

1. Field Of The Invention

The present invention relates to an apparatus for locating and anesthetizing peripheral nerves during the performance of a regional nerve blockade procedure. More particularly, the present invention relates to an apparatus including a remote foot pedal which enables independent, hands free, operation of the apparatus. Further, the foot pedal enables the operator to finely control the level of stimulus used to locate and stimulate a peripheral nerve.

2. Description Of The Prior Art

Today's consumer demands that medical care be not only efficacious, but cost-effective as well. These forces have had a dynamic changing effect on the field of anesthesia, and in particular on the practice of regional anesthesia.

The practice of regional anesthesia, the administration of anesthesia to a specific body region, is entering a renaissance. An increasing number of patients are receiving anesthetic nerve blocks during surgery, for the relief of post-operative pain, and for the extended relief of chronic pain. Numerous studies have shown that regional anesthesia is often preferable to the use of general anesthesia because of increased safety and patient satisfaction, excellent post-operative pain control, and a decrease in anesthesia costs.

The goal of all regional anesthesia techniques is to deliver a pool of local anesthetic into close contact with a peripheral nerve, thereby enabling neuronal blockade to occur. Typically, a syringe containing a solution of local anesthetic, with a needle attached to it, is utilized to perform the blockade of a peripheral nerve. Because the nerve to be blocked is not visible, various methods have been developed to insure that the needle is adjacent to the nerve before the solution of local anesthetic is injected.

The traditional method for ensuring that the needle is in close proximity to the nerve to be blocked involves eliciting paresthesia (a buzzing or tingling sensation reported by the patient to the physician). While the paresthesia technique usually produces a reliable blockade, one must often touch the nerve to elicit a response, which can cause permanent damage to the nerve. Further, a needle that passes even half a centimeter from the nerve frequently will not produce paresthesia and, yet, in many situations, this would be close enough to produce an effective block. Obviously, the success rate of a nerve block will be low when the patient gives an inaccurate report of paresthesia or when the patient is disoriented, sedated or otherwise not fully functional.

In an effort to increase the success rate of a nerve block, some anesthesiologists x-ray patients before administering an anesthetic solution to determine the exact location of the anesthesia needle vis-a-vis the target nerve. Although somewhat helpful, this technique is impractical, expensive, and not always readily available.

More recently, peripheral nerve stimulators, which forward an electrical stimulus to the anesthesia needle, have been used as a means of effectively locating peripheral nerves. Nerve localization via electrical stimulation is based on the fact that an electrical pulse can stimulate a motor nerve fiber to contract an innervated muscle or cause paresthesia in the case of sensory nerve stimulation.

When localizing a nerve using a nerve stimulator, an electrified anesthesia needle having a current of approximately 2–3 mA is placed within the tissue of the body in the vicinity of the nerve to be blocked. The needle is then slowly advanced as a stimulating probe until stimulation of the target nerve is achieved, as determined by visually detecting muscle contractions or by eliciting a report that the patient feels the stimulus. Once a response is observed, the current is gradually decreased as the needle is moved closer to the nerve, until nerve stimulation is obtained using a lower amperage current. Typically, response at a lower amperage (0.2–0.5 mA) assures that the tip of the needle is in close proximity to the nerve, therefore providing a reliable nerve blockade with injection of the local anesthetic.

Once a response has been observed in the 0.2–0.5 mA range, a small portion of the anesthetic dose is administered to the patient as a test dose to terminate the response of the nerve to the electrical pulse. The output current is then once again increased to assure that the cessation of the response is a result of the nerve blockade, rather than unintentional repositioning of the needle away from the nerve. If a nerve response is still absent after the output current has been increased, the anesthesia needle is deemed to be in the vicinity of the target nerve and the remaining dose of the local anesthetic solution is injected.

The same technique can be employed regardless of whether the nerve to be localized is motor or sensory. A description of this nerve localization technique is discussed in greater detail in Raj et al., "Use of the Nerve Stimulator for Peripheral Blocks", Regional Anesthesia, April-June 1980, pp. 14–21.

A debate has ensued among anesthesiologists as to whether the paresthesia technique or the peripheral nerve stimulation (PNS) technique is preferable. One obvious advantage of the PNS technique is that it causes minimal discomfort to the patients since the low stimulating currents that are used (0.2 to 2.0 mA) readily stimulate the larger A-alpha motor fibers resulting in painless muscle twitching. This is in contrast to the paresthesia technique which seeks to stimulate the C pain fibers, thereby causing varying degrees of pain or discomfort. The other advantage of PNS is that patient cooperation is not needed during the procedure, so that nerve blockade can be performed in an anesthetized patient. The incidence of nerve damage may also be decreased compared to the paresthesia technique since the probing needle does not have to touch or puncture the nerve. Further, the success rate of PNS is equal to or greater than the use of paresthesia.

However, manipulating the current of the generator by one anesthesiologist without additional help is very inconvenient and cumbersome or can cause unintentional repositioning of the needle.

Thus, one significant disadvantage, typically identified with the use of the PNS technique, is the frequent need for an entourage of helpers for the anesthesiologist to carry out the procedure. Because most anesthesiologists use a strictly sterile technique while performing a nerve block, the use of a nerve stimulator during administration of regional anesthesia is generally thought to require an extra person. While in a teaching institution this is usually not an important issue, in a busy private practice, where extra personnel are not readily available, it may present a significant disadvantage. Because PNS involves frequent changing of the current as the needle advances towards the nerve, there presently exists a significant divergence of opinion about the practicality of utilizing nerve stimulators for peripheral nerve blocks.

Examples of nerve stimulators for assisting in the administration of anesthesia may be found in U.S. Pat. No. 3,682,162 to Coyler and U.S. Pat. No. 4,515,168 to Chester et al. The Coyler patent generally describes a combined electrode and syringe needle which acts as a stimulation probe when the syringe needle is connected to an electrical supply.

The Chester et al. patent discloses a nerve stimulator which is clamped onto the syringe of a conventional syringe and anesthesia needle assembly. The unit contains a power supply, a pulse generating circuit, and a manually controlled current-adjusting potentiometer which allows the operator to adjust the current supplied to the needle.

Although the above-identified devices are effective in stimulating peripheral nerves and have been used in the practice of regional anesthesia, they have some significant disadvantages. As previously mentioned, when using these devices, an anesthesiologist must manually adjust the strength of the electrical current. This could potentially cause a number of problems. First, an attempt to manipulate the control knob will draw the anesthesiologist's attention away from the blockade procedure. This distraction may result in the needle being mis-positioned within the body or even result in permanent damage to the peripheral nerve. Alternatively, the requirement for an assistant to adjust the control knob can result in the misuse of scarce personnel.

Recently, a more advanced peripheral nerve stimulator has been disclosed in U.S. Pat. No. 5,284,153 to Raymond et al., which discloses a device that includes an anesthesia needle coupled to an electrical source, and a device for detecting nerve response to the electrical stimuli. The amount of current generated by the electrical source is automatically controlled so as to maintain the signal generated as a function of the response of the nerve to the stimuli. The closer the stimulating needle comes to the nerve, the higher the detected responses will be, which in turn will automatically decrease the electrical stimulus.

Although Raymond et al. solves some of the problems discussed above, this device has some inherent problems. First, its satisfactory performance requires the accurate placement of both the needle used to perform the block and the sensing unit which detects a muscle response. If the sensing unit is not placed at an appropriate location, then the apparatus will be unable to efficaciously locate the nerve.

Second, the Raymond et al. device is likely to be significantly more expensive and labor intensive due to its complexity. For example, the patent discloses the response detecting device in a form of electrodes similar to those used for electromyography, with a variable high-gain amplifier. The response signal is then converted into a digital signal and fed to a stimulus delivering device which utilizes a rather complicated, microcomputer based means for determining the amplitude of the next stimulus to be delivered. Therefore, these devices are not likely to be of a portable pocket size which is the case with modern PNS stimulators.

Finally, while automation may mean convenience, it may also present a disadvantage when the anesthesiologist has difficulty locating the nerve, requiring an increase in the stimulating current, such as in obese patients. In these instances, the operator must then switch to manual control, as described in the Raymond et al. disclosure, which brings back the same disadvantages inherent in older units, i.e., requires another person.

SUMMARY OF THE INVENTION

Therefore, the broad object of this invention is to provide an improved peripheral nerve stimulator having certain features similar to those currently available, but with foot pedal means for remotely controlling the amount of current delivered, thereby allowing an anesthesiologist to perform an unassisted nerve blockade.

Another object of the invention is to provide an improved peripheral nerve stimulator which enables the maintenance of sterility during the entire nerve blockade procedure.

A further object of the invention is to provide an improved peripheral nerve stimulator which enables an operator to infinitely adjust, within a selected range, the magnitude of electrical stimulus supplied to the anesthesia needle.

Still a further object of the invention is to provide for an improved peripheral nerve stimulator which does not require exact positioning of a response detecting means to ensure satisfactory performance of the blockade procedure.

Thus, the various features of the invention include an electrical stimulus generator for providing an electrical stimulus within a selected range. The generator has one or more control knobs for designating the selected range of the electrical stimulus. The invention is also adapted for accepting a syringe for storing and administering an anesthetic and a tube. The tube has a first end which is connected to the syringe and a second end which is adapted to accept an insulated anesthesia needle. One end of the syringe is formed for connecting to a disposable insulated anesthesia needle. An electronic cable connects the needle to the generator to provide electrical current to the needle. Also connected to the generator via a coupling cable is a remotely located foot-operated pedal. An operator can manipulate the pedal with his or her foot to both control and infinitely modify, within the initial selected range, the magnitude of the electrical stimulus. For example, if the anesthesiologist initially selects a maximum stimulus of 2 mA, then the range of the electrical stimulus will be between 0 mA and 2 mA. If the anesthesiologist selects 5 mA, then the available range will be between 0 mA and 5 mA. Use of the remote foot pedal leaves the operator's hands free for the nerve blockade procedure, so that an assistant is not required.

The foot pedal is not spring loaded, but works on the leverage principle. The operator can pivot the pedal to a desired position, corresponding to a selected stimulus level, and then remove his or her foot from the pedal. The position of the pedal will not change when the foot is subsequently removed, therefore the stimulus level will remain constant until the pedal is manipulated once again.

The invention also discloses a method for utilizing the inventive apparatus. According to the inventive method, the apparatus is used by designating a selected range for an electrical stimulus. Next, an electrical stimulus is generated within the selected range. The anesthesia needle is then inserted into the tissue of the body in the vicinity of the nerve to be located, and an operator looks for a response by the nerve (i.e., twitch of the muscles innervated by the nerve being blocked, or a paresthesia sensation in the sensory distribution of the nerve sought). If a response is observed, the output current of the generator is decreased by manipulating the remote foot pedal and the needle is further advanced towards the nerve until a response of equal intensity is once again obtained. The precise placement of the needle is assured by decreasing the electrical output current of the nerve stimulator as the needle approaches the peripheral nerve. If the response is lost upon further advancement of the needle, it can be obtained by either withdrawing the needle or by increasing the output current using the foot pedal control.

If an adequate response is observed with a current 0.1 to 0.5 mA (Raj), the nerve is deemed to have been "found" or located. A small test portion of the anesthetic is then administered to the patient as a test dose to terminate the response of the nerve to the electrical pulse. After an amount of time sufficient for the anesthetic to take effect, the output current is once again increased to 2–3 mA to assure that the cessation of the response is the result of effective nerve blockade, rather than the unintentional repositioning of the needle away from the nerve. If no further nerve response is observed, the anesthesia needle is deemed to be in the vicinity of the target nerve and the remaining dose of anesthetic is injected.

Although the above-described technique requires frequent current changes for the best results, the described method and adaptation of the nerve stimulator of the present invention allows a solo anesthesiologist to achieve a totally independent, comfortable, and efficacious performance of the nerve blockade.

BRIEF DESCRIPTION OF THE DRAWING

Various objects, features and attendant advantages of the present invention will be more fully appreciated as the same becomes better understood from the following detailed description of the present invention when considered in connection with the accompanying drawings, in which.

DETAILED DESCRIPTION OF THE INVENTION

Figure 1:
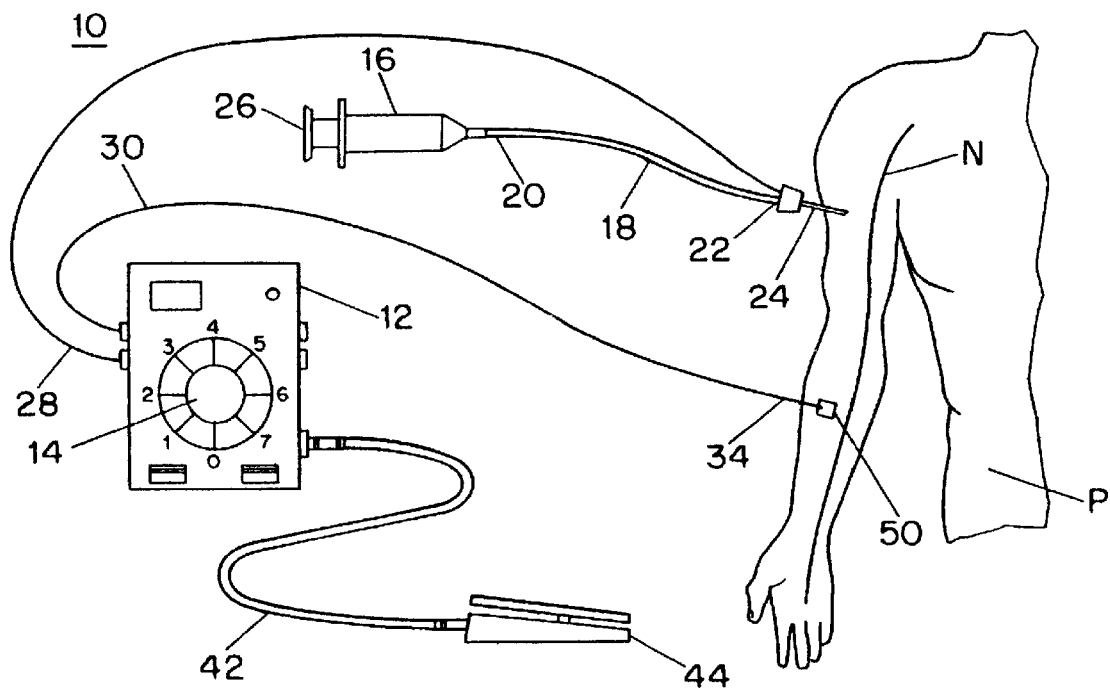
FIG. 1 shows a perspective view of the present invention.
Figure 2:
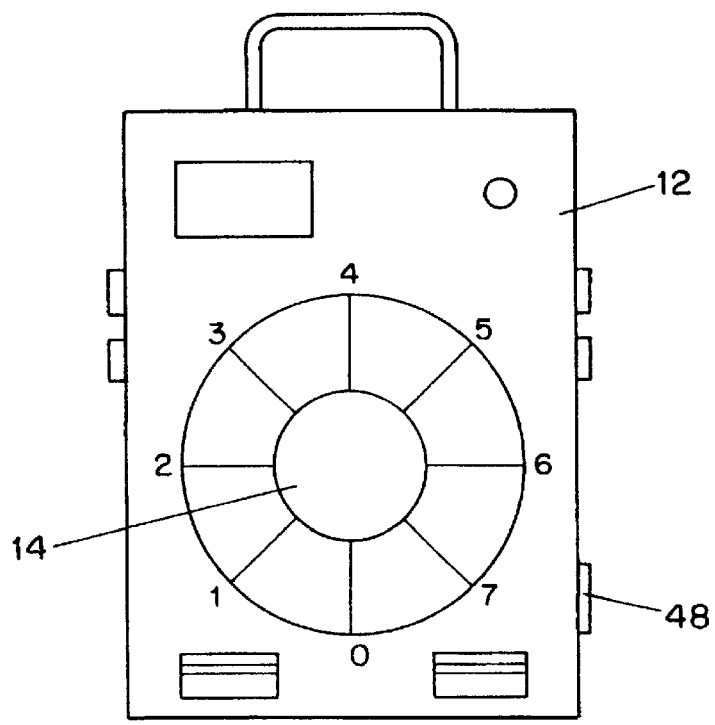
FIG. 2 shows a top view of a peripheral nerve stimulator utilized in the present invention.
Figure 3:
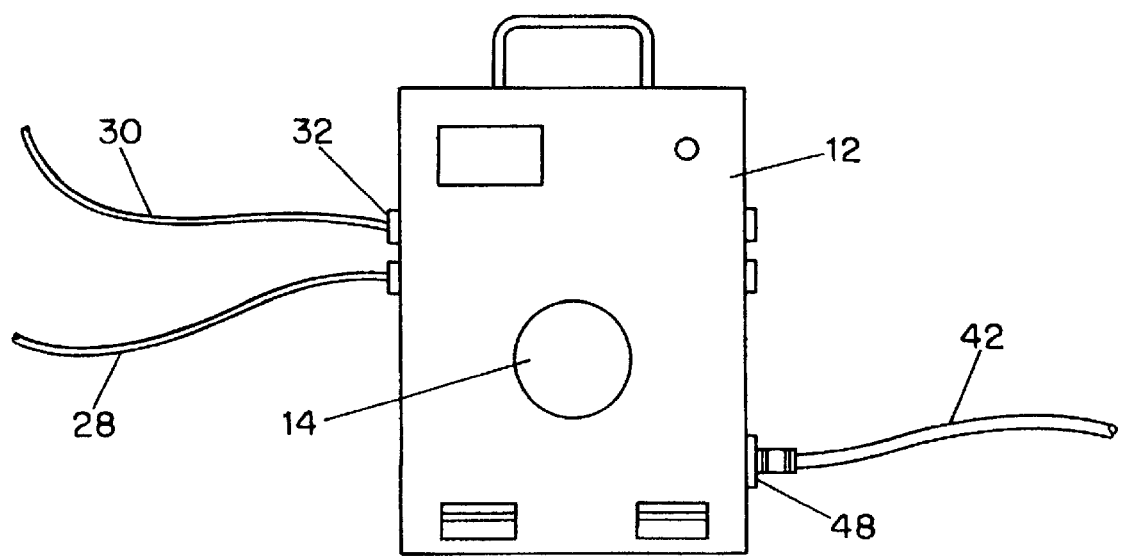
FIG. 3 shows the peripheral nerve stimulator of FIG. 2 including a foot pedal cable, a stimulus cable and a ground cable.

With reference to FIGS. 1–3, there is shown a peripheral nerve stimulator apparatus 10 having an electrical stimulus generator 12 for providing an electrical stimulus within a selected range. The generator 12 has one or more control knobs 14 for designating the selected range of the electrical stimulus. One preferred generator used in the present invention is a "DUAL STIM PLUS" nerve stimulator, model NS-2CA, produced by Life-Tech, Inc., in Houston, Tex. However, any analog or digital nerve stimulator currently on the market can be modified to operate with the present invention.

Figure 6:
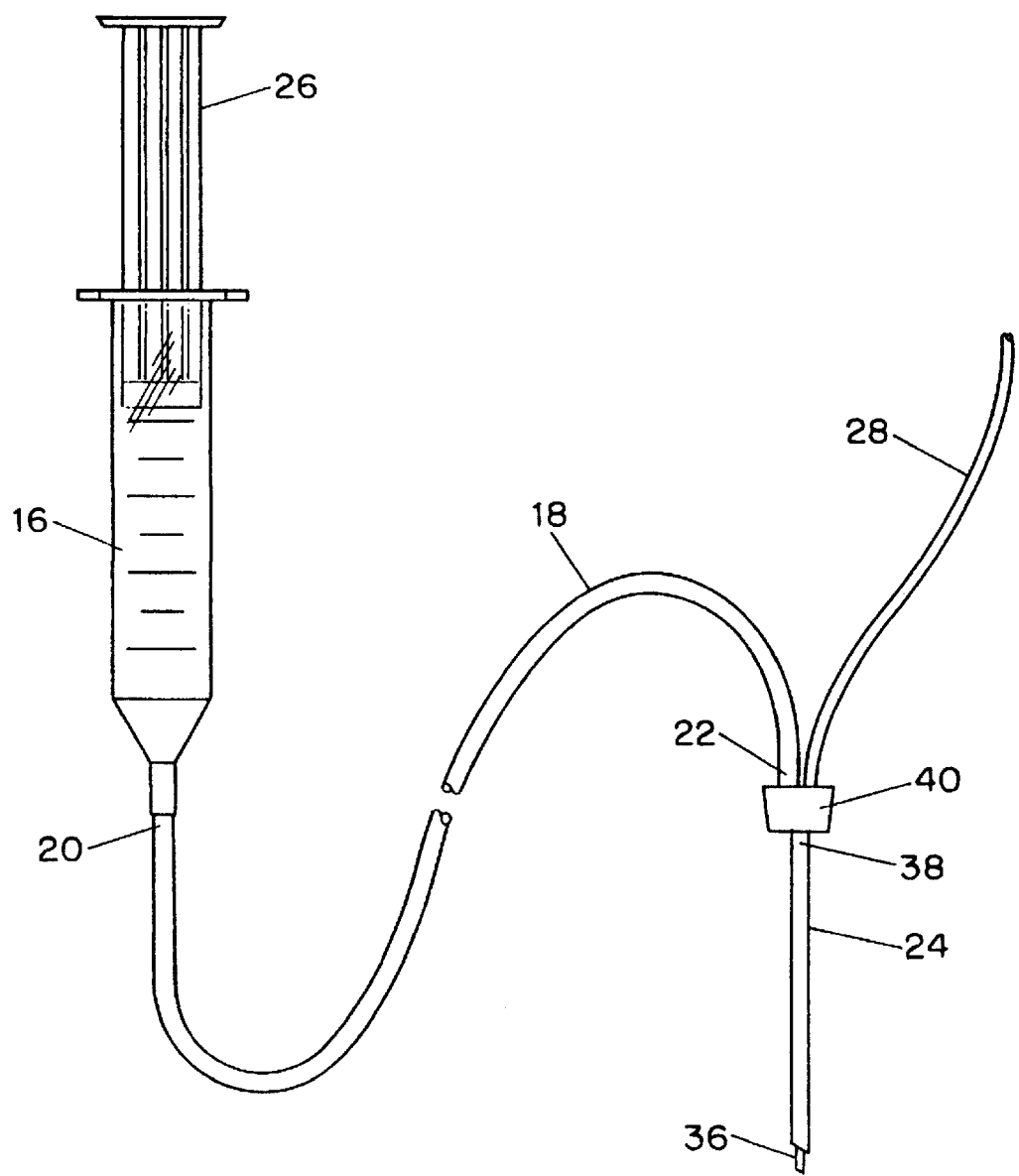
FIG. 6 shows a side view of a syringe and anesthesia needle utilized in the present invention.

Referring to FIGS. 1 and 6, the apparatus 10 is adapted for accepting a syringe 16 for storing and administering an anesthetic and a tube 18. The tube has a first end 20 which is connected to the syringe 16 and a second end 22 which is adapted to accept an insulated anesthesia needle. The syringe 16 includes a plunger 26 for forcing the anesthetic into the tube 18. Referring to FIGS. 1 and 3, an electronic cable 28 connects the needle 24 to the generator 12 for delivering the electrical stimulus to the needle 24, thereby allowing the electrical stimulus to be delivered to a nerve N.

The apparatus 10 also has a grounding wire 30 having a first end 32 connected to the stimulus generator 12 and a second end 34 connected to a patient P. The grounding wire 30 enables the electrical connection to be completed.

Referring to FIG. 6, the anesthesia needle 24 has a first end 36 which is inserted into the patient P and a second end 38 having a hub 40. The hub 40 is adapted for accepting the second end 22 of the tube 18 and the electronic connector 28.

Referring to FIGS. 1, 3, 4 and 5, also connected to the generator 12 via a coupling cable 42 is a remotely located foot-operated pedal 44. An operator can manipulate the pedal 44 with his or her foot to both control and infinitely modify, within the selected range, the magnitude of the electrical stimulus. For example, if an anesthesiologist utilizes the control knob 14 (FIG. 2) to select a maximum stimulus of 2 mA, then the range of the electrical stimulus can be modified between 0 mA and 2 mA by moving the position of the foot pedal 44. If the anesthesiologist selects 5 mA with the control knob 14, then the available range will be between 0 mA and 5 mA. Use of the remote foot pedal 44 leaves the operator's hands free for the nerve blockade procedure, thereby obviating the need for an assistant. Further, use of the pedal allows the anesthesiologist to concentrate solely on the position of the needle 24 and the patient's P nerve response.

Figure 4:
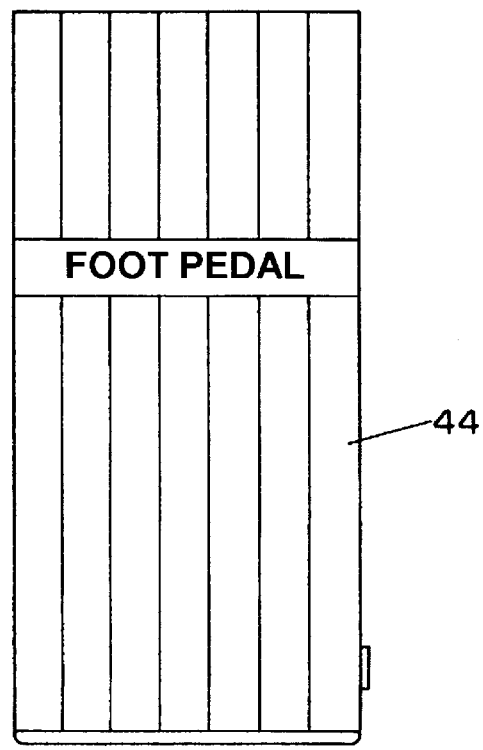
FIG. 4 shows a top view of a foot pedal utilized in the present invention.
Figure 5:
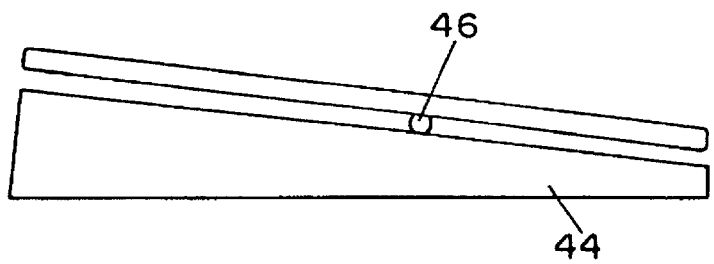
FIG. 5 shows a side view of the foot pedal in FIG. 4.

Referring to FIGS. 4 and 5, the foot pedal 44 is not spring loaded, but works on the leverage principle. The operator can pivot the pedal around a pivot point 46 to the desired position, one which corresponds to a desired stimulus level, and then remove his or her foot from the pedal 44. The position of the pedal 44 will not change when the foot is subsequently removed, therefore, the stimulus level will remain constant until the pedal 44 is once again manipulated.

One preferred foot pedal 44 is a "KORG" one-channel volume pedal, model KVP-001. However, any foot controlled variable resistor pedal can be used to achieve the same results.

Referring to FIG. 3, the stimulus generator 12 has been modified by the addition of a coupling jack 48 so that the foot pedal 44 can be electronically coupled to the generator 12. The addition of the jack 48 is an essential feature of the invention because it enables the operator to modify the generated stimulus by manipulating the foot pedal 44.

Referring to FIG. 1, before starting the procedure, a grounding pad 50 is placed on a patient's P body. The grounding pad 50 is connected to the grounding wire 30, which in turn is connected to the stimulus generator 12. The operator then turns the control knob 14 to designate a desired electrical stimulus range. Next, a switch is engaged in order to send electrical power to the stimulus generator 12, thereby generating an electrical stimulus within the selected range. The first end 36 of the anesthesia needle 24 is then inserted into the tissue of the patient P in the vicinity of the nerve N to be located. After the needle 24 has been inserted in the vicinity of the nerve N, the operator depresses the foot pedal 44 to increase the magnitude of the electrical stimulus. The operator then looks for a response by the nerve N (i.e., twitch of the muscles innervated by the nerve being blocked, or a paresthesia sensation in the sensory distribution of the nerve sought). If a response is observed, the output current of the generator 12 is decreased by manipulating the remote foot pedal 44 and the needle 24 is further advanced towards the nerve N until a response of equal intensity is once again obtained. The precise placement of the needle 24 is assured by decreasing the electrical output current of the nerve stimulator 12 as the needle 24 approaches the peripheral nerve N. If the response is being lost by further advancement of the needle 24, it is sought again by withdrawing the needle 24 or by manipulating the foot pedal 44 to increase the output current sent to the anesthesia needle 24.

After an adequate response is observed with a current 0.1 to 0.5 mA (Raj), the nerve N is deemed to have been "found"

or located. A small test portion of the anesthetic is then administered to the patient as a test dose to terminate the response of the nerve to the electrical stimulus. After sufficient time is allowed to elapse in order for the anesthetic to take effect, the output current is once again increased to 2–3 mA to assure that the cessation of the response is the result of effective nerve blockade, rather than the unintentional repositioning of the needle 24 away from the nerve N. If no further nerve response is observed, the anesthesia needle 24 is deemed to be in the vicinity of the target nerve N and the remaining dose of anesthetic is injected.

EXPERIMENTAL TESTS

To evaluate the performance of the present invention, various experiments were performed.

In vivo experiments were performed on three volunteers. A hand-held 22 G insulated needle, which served as stimulating probe was attached to a modified nerve stimulator "DUAL STIM PLUS", model NS-2CA, Life-Tech, Inc., Houston, Tex. Then, the needle was introduced through the skin in the femoral fossa, aiming towards the femoral nerve. Once the needle was under the skin, the foot pedal was pressed to set the stimulating current output to 2 mA. Once twitches in the quadriceps muscle were observed, the current was gradually decreased and the needle further advanced. These maneuvers were repeated until the twitches were observed at a current of 0.2 mA. A test dose of 3 cc Lidocaine 1% injected through the needle resulted in cessation of the twitch response. To confirm that adequate nerve blockade had been performed, the current of the nerve stimulator was once again increased to 2 mA by stepping on the foot pedal. When no response was observed at 2 mA, the rest of the anesthetic was then injected. Using the foot pedal to control the output of the nerve stimulator enabled the anesthesiologist to perform, unassisted, a safe and efficacious nerve blockade procedure.

The introduction of the foot pedal 44 allows the apparatus 10 of the invention to function in a more precise manner than earlier PNS models, and provides for more accurate current control, with an infinite number of ranges (0.1 to 10 mA). The amperage ranges were verified through use of an amperometer serially connected in line with the circuit. Thus, the desired nerve N can be effectively located while providing a maximum level of comfort for the patient.

It is to be understood that the foregoing is considered as illustrative only of the principles of the invention. Therefore, within the scope of the appended claims, the invention may be practiced otherwise than as specifically described herein.

We claim:

1. A peripheral nerve stimulator apparatus for a nerve blockade procedure, comprising:
    a generator for providing an electrical stimulus within a selected amperage range, the generator having means for designating the selected range;
    a needle;
    means for storing and delivering anesthesia to the needle;
    means for delivering an electrical stimulus to the needle; and
    a remotely located foot pedal connected to the generator for manually controlling the magnitude of the electrical stimulus delivered to the needle by an operator's foot, wherein the foot pedal is of the leveraged type whereby the magnitude of the electrical stimulus is not changed if the operator's foot is removed from the foot pedal and wherein the operator can control and infinitely modify the electrical stimulus within the selected range by manipulation of the foot pedal, thereby leaving the operator's hands free for the nerve blockage procedure, whereby the operator can carry out the nerve blockage procedure without the need for an assistant to control the magnitude of the electrical stimulus.

2. The apparatus of claim 1 wherein the generator is a nerve stimulator.

3. The apparatus of claim 1 wherein the designating means are control knobs for selecting the range of the amperage to be utilized.

4. The apparatus of claim 1, wherein the means for delivering the anesthesia is a tube having a first end for connecting to the syringe and a second end adapted for connecting to the needle.

5. The apparatus of claim 1, wherein the means for delivering an electrical stimulus to the needle is an electrical connector having a first end for connecting to the generator and a second end for connecting to the needle.

6. The apparatus of claim 1, wherein the foot pedal is connected to the generator through a coupling cable.

7. The apparatus of claim 1, wherein the foot pedal is a one-channel volume pedal.

8. The apparatus of claim 1, wherein the foot pedal includes pivot means for facilitating positioning of the pedal.

9. A method for locating and anesthetizing a peripheral nerve b an unassisted operator, said method comprising the steps of:
    (a) designating a selected range for an electrical stimulus;
    (b) generating the electrical stimulus of a magnitude within the selected range by manipulating a foot pedal, wherein the foot pedal is of a leveraged type whereby the magnitude of the electrical stimulus is not changed if the operator's foot is removed from the foot pedal;
    (c) delivering the electrical stimulus to a nerve using an insulated anesthesia needle;
    (d) modifying the magnitude of the next stimulus to be delivered to the nerve by manipulation of the foot pedal;
    (e) observing the response of the nerve to the stimulus to determine the distance of the needle from the nerve;
    (f) repositioning the needle in relation to the nerve;
    (g) delivering the next stimulus to the nerve using the needle;
    (h) repeating steps (b) through (g) until the needle is in close proximity to the nerve; and
    (i) delivering a drug through the needle to anaesthetize the nerve, whereby the operator can carry out the locating and anesthetizing of the nerve without the need for an assistant to control the magnitude of the electrical stimulus.

10. The method of claim 9, wherein steps (b) through (g) are repeated until a response is observed at a stimulus level within the range of about 0.1 mA to about 0.5 mA.

11. The method of claim 9, wherein steps (b) through (g) are repeated until a response is observed at a stimulus level of not more than 0.2 mA.

* * * * *

UNITED STATES PATENT AND TRADEMARK OFFICE
CERTIFICATE OF CORRECTION

PATENT NO.   : 5,830,151
DATED        : November 3, 1998
INVENTOR(S)  : Hadzic et al.

It is certified that error appears in the above-indentified patent and that said Letters Patent is hereby corrected as shown below:

<u>IN THE CLAIMS:</u>

Column 7, line 64, after "pedal" insert --,-- (a comma)

Column 8, line 29, change "b" to --by--

Column 8, line 49, change "anaesthetize" to --anesthetize--

Signed and Sealed this

First Day of June, 1999

Attest:

Attesting Officer

Q. TODD DICKINSON

*Acting Commissioner of Patents and Trademarks*